US011827551B2

(12) United States Patent
Ogura et al.

(10) Patent No.: US 11,827,551 B2
(45) Date of Patent: Nov. 28, 2023

(54) METHOD AND SYSTEM FOR RECOVERING MICROPLASTICS FROM WATER

(71) Applicant: Novelgen Co., Ltd., Nagahama (JP)

(72) Inventors: Atsushi Ogura, Nagahama (JP);
Yoshihiro Kawada, Nagahama (JP);
Yui Sawada, Nagahama (JP);
Hiromasa Tabata, Nagahama (JP)

(73) Assignee: Novelgen Co., Ltd., Nagahama (JP)

( * ) Notice: Subject to any disclaimer, the term of this patent is extended or adjusted under 35 U.S.C. 154(b) by 0 days.

(21) Appl. No.: 18/004,978

(22) PCT Filed: Oct. 26, 2022

(86) PCT No.: PCT/JP2022/039814
§ 371 (c)(1),
(2) Date: Jan. 10, 2023

(87) PCT Pub. No.: WO2023/074716
PCT Pub. Date: May 4, 2023

(65) Prior Publication Data
US 2023/0192519 A1    Jun. 22, 2023

(30) Foreign Application Priority Data
Oct. 26, 2021 (JP) .................. 2021-175090

(51) Int. Cl.
*C02F 3/32* (2023.01)
*C02F 1/28* (2023.01)
*C12P 19/04* (2006.01)
*C12N 1/12* (2006.01)

(52) U.S. Cl.
CPC .............. *C02F 3/322* (2013.01); *C02F 1/28* (2013.01); *C12N 1/12* (2013.01); *C12P 19/04* (2013.01)

(58) Field of Classification Search
CPC ... C02F 3/322; C02F 1/28; C12N 1/12; C12P 19/04
USPC ........................................................ 210/602
See application file for complete search history.

(56) References Cited

FOREIGN PATENT DOCUMENTS

| JP | S49-45553 A | 5/1974 |
|---|---|---|
| JP | 6955292 B1 | 10/2021 |
| WO | WO 2017/106941 A1 * | 6/2017 |

OTHER PUBLICATIONS

Machine-generated English translation of WO 2017/106941, generated on May 16, 2023.*
Atsushi Ogura, Technology for Removing Microplastics Using Microalgae, Convertech, Jul. 15, 2020, vol. 48, 7, 568, pp. 2-5.

* cited by examiner

*Primary Examiner* — Fred Prince
(74) *Attorney, Agent, or Firm* — Muncy, Geissler, Olds & Lowe, P.C.

(57) ABSTRACT

To provide a new technique for efficiently recovering microplastics from water to be treated, in which problems of conventional techniques such as large energy consumption are solved. A method for recovering microplastics from water to be treated containing the microplastics, the method comprising a step of allowing algae having microplastic adsorption and recovery ability to be present in the water to be treated, in which the algae are algae that secrete a sticky substance, and an amount of a sticky substance secreted by the algae is such that a volume of a sticky substance secreted to an outside of cells is 0.25 times or more and 100 times or less compared to a cell volume.

6 Claims, 12 Drawing Sheets

FIG. 10

STICKY SUBSTANCE SECRETED BY MICROALGAE MEASUREMENT METHOD

- SILICON SHEET WAS ATTACHED TO CENTER OF GLASS SLIDE TO PREPARE GLASS SLIDE FOR MEASURING MUCILAGE (RIGHT FIGURE)

- 10 μl OF MICROALGAE CULTURE SOLUTION CULTURED ON SILICON SHEET WAS ADDED

- 10 μl OF INDIA INK DILUTED 5-FOLD WAS ADDED. INDIA INK AND MICROALGAE CULTURE SOLUTION WERE MIXED WELL. COVER GLASS WAS PLACED. AND AREA OF EXTRACELLULAR MUCILAGE WAS MEASURED UNDER MICROSCOPIC ENVIRONMENT

- AS FOR CELL VOLUME, EACH ALGAE WAS APPROXIMATED BY ELLIPTIC CYLINDER, ELLIPSE, RECTANGULAR PARALLELEPIPED, AND COMBINATION THEREOF, AND CELL VOLUME V ACCORDING TO FOLLOWING FORMULA WAS OBTAINED

- ELLIPTIC CYLINDER  $V = \pi/4*abh$  a: MAJOR AXIS OF ELLIPSE, b: MINOR AXIS OF ELLIPSE, h: HEIGHT OF ELLIPTIC CYLINDER ELLIPSOID  $V = \pi/6*ab2$  a: MAJOR AXIS OF ELLIPSE, b: MINOR AXIS OF ELLIPSE RECTANGULAR PARALLELEPIPED  $V = abh$  a: LENGTH, b: WIDTH, h: HEIGHT

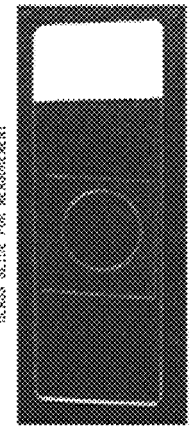

GLASS SLIDE FOR MEASUREMENT

FIG. 11
Pyrocystis fusiformis
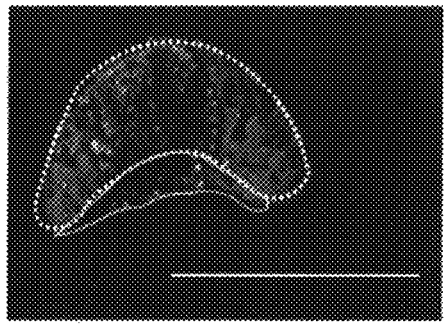
Euglena mutabilis
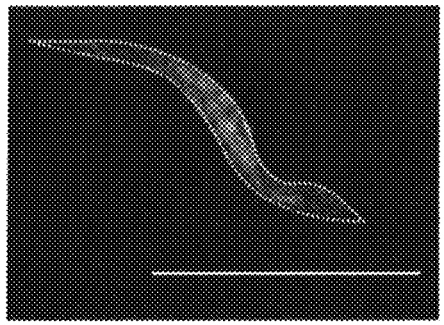
Closterium ehrenbergii
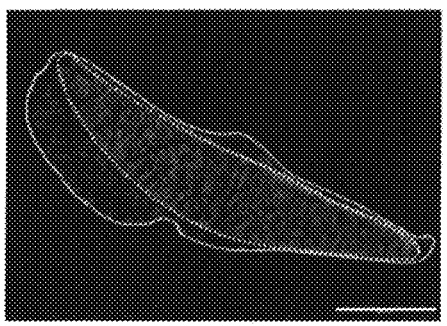
Calothrix parasitica
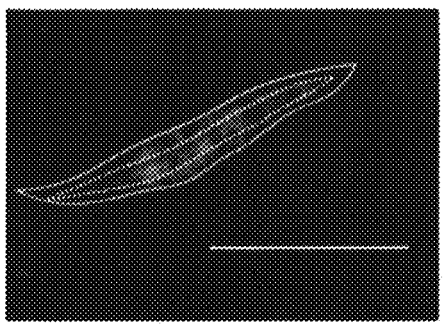
Achnanthes kuwaitensis
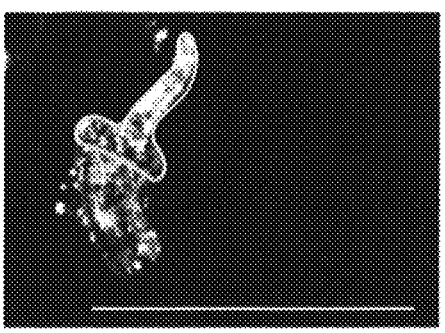
Chlorarachnion reptans
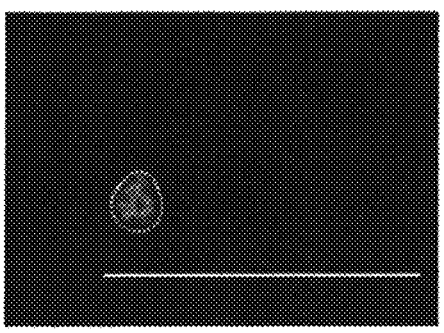
LEFT ILLUSTRATES scale bar = 100 μm   RIGHT COLUMN ILLUSTRATES scale bar = 50 μm
line = MUCILAGE INTERFACE              dot line = CELL SURFACE

METHOD AND SYSTEM FOR RECOVERING MICROPLASTICS FROM WATER

TECHNICAL FIELD

The present invention relates to a method and system for recovering microplastics from water (e.g., seawater or river water).

BACKGROUND ART

Plastic is one of the indispensable materials in life. On the other hand, microplastics generated when the plastic is, for example, broken has a serious problem on the environment and also threatens the ecological system. It is said that microplastics enter human bodies from food chains or various routes and accumulates little by little.

As a technique for recovering microplastics, a technique for removing microplastics using microalgae has been proposed (Non-Patent Literature 1).

CITATION LIST

Non-Patent Literature

Non-Patent Literature 1: Convertech, July 2020, pp. 2-5

SUMMARY OF INVENTION

Technical Problem

The present inventors have attempted to remove microplastics in accordance with Non Patent Literature 1, and have found that an event in which microplastics cannot be stably recovered over a long period of time occurs. Therefore, an object of the present invention is to provide a means capable of stably recovering microplastics over a long period of time.

Solution To Problem

The present inventors have examined countless conditions such as the type, amount and size of algae and various culture conditions, have found that the above-described problem can be solved when the volume of sticky substance secreted to the outside of a cell is within a predetermined range compared to the cell volume, and have completed the present invention. Specifically, the details are as follows.

The present invention (1) is a method for recovering microplastics from water to be treated containing the microplastics, the method comprising a step of allowing algae having microplastic adsorption and recovery ability to be present in the water to be treated, in which the algae are algae that secrete a sticky substance, and an amount of a sticky substance secreted by the algae is such that a volume of a sticky substance secreted to an outside of cells is 0.25 times or more and 100 times or less compared to a cell volume.

The present invention (2) is the method of the invention (1), in which the sticky substance is a polysaccharide.

The present invention (3) is the method of the invention (1) or (2), in which the algae are at least one species selected from diatoms, dinoflagellate algae, Chlorarachniophyte algae, green algae, red algae, conjugating algae, Euglena algae, and blue-green algae.

The present invention (4) is a system for recovering microplastics from water to be treated containing the microplastics, the system utilizing algae having microplastic adsorption and recovery ability when the microplastics are recovered from the water to be treated, in which the algae are algae that secrete a sticky substance, and an amount of a sticky substance secreted by the algae is such that a volume of a sticky substance secreted to an outside of cells is 0.25 times or more and 100 times or less compared to a cell volume.

The present invention (5) is the system of the invention (4), in which the sticky substance is a polysaccharide.

The present invention (6) is the system of the invention (4) or (5), in which the algae are at least one species selected from diatoms, dinoflagellate algae, Chlorarachniophyte algae, green algae, red algae, conjugating algae, Euglena algae, and blue-green algae.

Advantageous Effects of Invention

According to the present invention, it is possible to provide a means capable of stably recovering microplastics over a long period of time.

BRIEF DESCRIPTION OF DRAWINGS

FIG. 10 is a diagram illustrating a procedure for measuring the amount of sticky substance secreted by algae.

FIG. 11 is an enlarged photograph of various algae used in Examples.

DESCRIPTION OF EMBODIMENTS

<<Method for Recovering Microplastics>>

Figure 1:
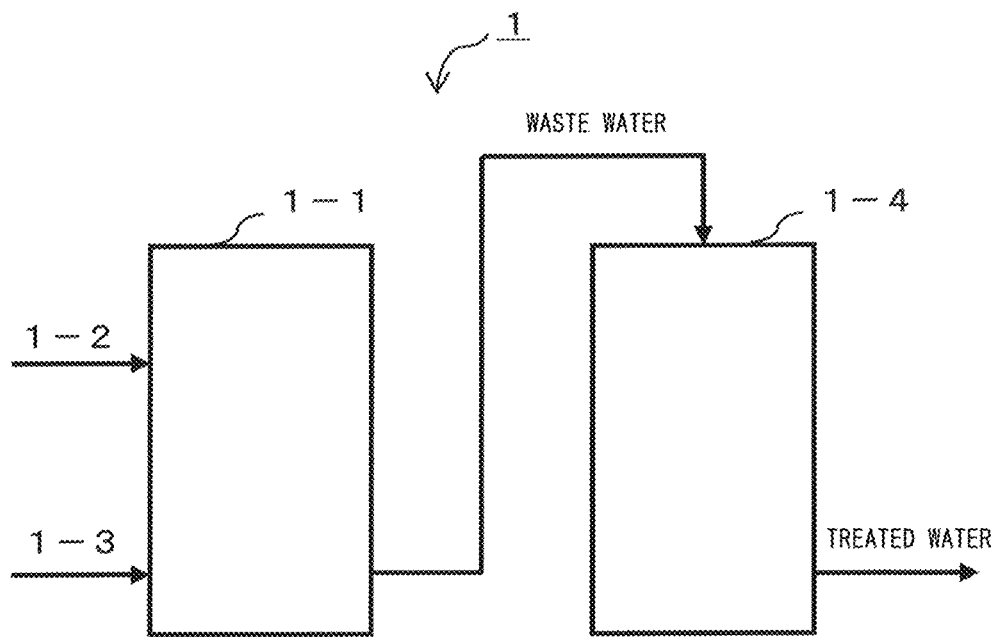
FIG. 1 is a conceptual diagram illustrating an example of a microplastic recovery system.

The present invention is a method for recovering microplastics from water to be treated containing the microplastics, the method comprising a step of allowing algae having microplastic adsorption and recovery ability to be present in the water to be treated, in which the algae are algae that secrete a sticky substance, and an amount of a sticky substance secreted by the algae is such that a volume of a sticky substance secreted to an outside of cells is 0.25 times or more and 100 times or less compared to a cell volume. Each component will be described in detail below.

<Water To Be Treated>

The water to be treated is not particularly limited, and, for example, water in which microplastics are present or may be present, which includes seawater, fresh water, brackish water, and other water. More specific examples thereof include raw water in preparing water (e.g., seawater for aquaculture, fresh water for aquaculture, ballast water, drinking water, and other water) which may be ingested by or come into contact with humans or animals.

<Microplastics>

The term "microplastics" as used in the present invention refers to particles having a size of 0.1 μm or more and 5000 μm or less (maximum length portion). However, the plastics which are present (or may be present) in the water to be treated, which is an object to be treated, may contain not only microplastics but also plastic particles having a particle size of less than 0.1 μm or more than 5000 μm. The actual microplastics are that most of the microplastics (e.g., 80% or more, 90% or more, or 95% or more of the total number of particles) are, for example, 0.1 μm or more, 0.5 μm or more, 1 μm or more, 2 μm or more, 3 μm or more, 4 μm or more, 5 μm or more, 6 μm or more, 7 μm or more, 10 μm or more, 50 μor more, 100 μm or more, 500 μm or more, 1000 μm or more, 2500 μm or more; 2500 μm or less, 1000 μm or less, 500 μm or less, 100 μm or less, 50 μm or less, 10 μm or less, 9 μm or less, 8 μm or less, 7 μm or less, 6 μm or less, 5 μm or less, 4 μm or less, or 3 μm or less (maximum length portion). Note that, as is well known, microplastics include primary microplastics (plastics manufactured in micro-size: for example, utilized in capsules for facial cleansers, softeners, and slow-release fertilizers) and secondary microplastics (large plastics crushed and fragmented into micro-size in natural environments).

<Algae>

The term "algae having microplastic adsorption and recovery ability" as used in the present invention refers to algae capable of reducing the concentration of microplastics in water to be treated when algae is allowed to be present by a predetermined amount (e.g., 10%, 20%, 30%, 40%, 50%, 60%, 70%, 80%, 90%, or 95%) or more compared to the concentration of microplastics in water to be treated when algae is not allowed to be present. Algae that secrete sticky substances include diatoms and brown algae belonging to Stramenopiles, dinoflagellate algae belonging to Alveolata, Chlorarachniophyte algae belonging to Rhizaria, green algae and red algae belonging to Archaeplastida, conjugating algae, Euglena algae belonging to Excavata, and blue-green algae belonging to eubacteria. Microalgae are known to release various mucilaginous substances to the outside of the cells. Sticky substances are typically polysaccharides, and are, for example, substances such as red algae such as tengusa, agarose or porphyran in the case of conjugating algae, or alginic acid or a fucose-containing polysaccharides in the case of brown algae such as kelp. Among various types of diatoms, Skeletonema tropicum is particularly preferable. Blue-green algae and green algae are preferable in that the growth rate of the algae is excellent. Further, since Euglena has flagella, it is preferable in that Euglena can actively adsorb microplastics.

Examples of the other algae also include: algae (e.g., brown algae) having a physical structure (e.g., a porous structure or a concave-convex structure) that traps microplastics; and algae charged with a charge opposite to that of microplastics. For example, microalgae vary in shape and size, and there are porous algae having a large surface area and those forming a filamentous colony. Such a structure also has the function of entangling microplastics. Unlike algae having sticky substances, such algae are less likely to undergo structural changes due to environmental changes or other changes, and thus are excellent in that trapped microplastics can be stably retained.

As the algae used for removing microplastics, one type selected from the above-described algae may be used, or two or more specific types of algae may be used in combination.

For example, combining diatoms and algae (e.g., blue-green algae and green algae) having a growth rate higher than that of the diatoms allows to sufficiently obtain the adsorption effect of microplastics even in the initial stage of culture.

Combining diatoms and algae (e.g., dinoflagellates and brown algae) having a size larger than that of the diatoms allows to sufficiently obtain an adsorption effect of microplastics having a larger size, which are difficult to be adsorbed by diatoms.

The size of the algae is not particularly limited. However, in view of the fact that the size of the microplastics to be treated is 0.1 μm or more and 5000 μm or less, the size is preferably 5000 μm or more (e.g., in the case of connected or clustered algae, the size of the connected or clustered algae). However, the size of the algae may be allowed to depend on the main size of microplastics present in the water to be treated, and in this case, the assumed size of the algae is, for example, 0.1 μm or more, 1 μm or more, 2 μm or more, 5 μm or more, 10 μm or more, 50 μm or more, 100 μm or more, 500 μm or more, 1000 μm or more, 2500 μm or more, 5000 μm or less, 2500 μm or less, 1000 μm or less, 500 μm or less, 250 μm or less, 100 μm or less, 50 μm or less, 25 μm or less, 20 μm or less, 10 μm or less, 5 μm or less, or 1 μm or less. Note that the "size" here refers to the maximum diameter portion (e.g., in the case of rod-shaped algae, the long diameter portion). Algae having various sizes are present in the system, and the "size" here refers to an average value of the sizes of 100 algae obtained at random.

In addition, the amount of the sticky substance secreted by the algae is preferably such that the volume of the sticky substance secreted to the outside of the cells is 0.25 times or more and 100 times or less compared to the cell volume. Within this range, it is possible to provide a means capable of stably recovering microplastics over a long period of time. Note that the method for measuring the volume is as follows. 10 μL of a microalgae culture solution cultured on a glass slide is added. 10 μL of India ink diluted 5-fold was added, the India ink and the microalgae culture solution were mixed well, a cover glass was placed, and the cell volume of microalgae and the volume of extracellular mucilage were measured under a microscopic environment. In accordance with the method of Kishimoto et al. {Kishimoto N., Ichise S., Suzuki K., Yamamoto C.: Analysis of long-term variation in phytoplankton biovolume in the northern basin of Lake Biwa. Limnology 14: 117-128(2013)}, each algae was approximated by an elliptic cylinder, an ellipse, a rectangular parallelepiped, and a combination thereof, and the cell volume was calculated. With respect to the extracellular mucilage volume, the volume including the portion not stained with India ink was calculated and the extracellular mucilage volume was obtained by dividing the cell volume. FIG. 10 is a diagram illustrating the above procedure. Algae having various sizes are present in the system, and the "amount" here refers to an average value of the sizes of 100 algae obtained at random.

The cell increase rate of algae used for removal of microplastics is preferably 250% or more, more preferably 300% or more, and even more preferably 400% or more. When the cell increase rate of the algae is within the above range, the sticky substance is rapidly secreted after culture, and thus the adsorption effect of microplastics can be exhibited at an early stage after the culture. The cell increase rate is calculated according to the following conditions and calculation formula.

<Culture Conditions>

The culturing of algae is carried out in 200 ml of medium (f/2, with the exception that the sodium nitrate is changed to 750 mg/L, which is 10 times the normal concentration). Table 1 illustrates the components of the medium (f/2). Table 2 illustrates the components of f/2 metals contained in the medium (f/2).

TABLE 1

| f/2 | |
|---|---|
| $NaNO_3$ | 75 mg |
| $NaH_2PO_4 \cdot 2H_2O$ | 0.6 mg |
| Vitamin $B_{12}$ | 0.05 μg |
| Biotin | 0.05 μg |
| Thiamine HCl | 10 μg |
| $Na_2SiO_3 \cdot 9H_2O$ | 1 mg |
| f/2 metals | 0.1 mL |
| Seawater | 99.9 mL |

TABLE 2

| f/2 metals | |
|---|---|
| $Na_2EDTA \cdot 2H_2O$ | 440 mg |
| $FeCl_3 \cdot 6H_2O$ | 316 mg |
| $CoSO_4 \cdot 7H_2O$ | 1.2 mg |
| $ZnSO4 \cdot 7H_2O$ | 2.1 mg |
| $MnCl_2 \cdot 4H_2O$ | 18 mg |
| $CuSO_4 \cdot H_2O$ | 0.7 mg |
| $Na_2MoO_4 \cdot 2H_2O$ | 0.7 mg |
| Distilled Water | 100 mL |

(Cell Increase Rate)

Each algae is cultured using the above-described medium. The number of cells before culture is, for example, 5000 to 20000 cells/ml, and typically 10000 cells/ml. Using an ultraviolet-visible spectrophotometer, the absorbance at a wavelength of 490 nm is measured 6 hours and 3 days after the start of the culture, respectively. The cell increase rate is calculated according to the following formula:

Cell increase rate=(absorbance measured after 3 days)/(absorbance measured after 6 hours)×100

Table 3 illustrates the cell increase rates obtained for the eight types of algae.

TABLE 3

| | | Absorbance | | Cell |
| Classification of Algae | Species Name | After 6 hours | After 3 days | Increase Rate |
|---|---|---|---|---|
| Diatoms | Achnanthes kuwaitensis | 0.1 | 0.28 | 280.0 |
| Diatoms | Skeletonema tropicum | 0.11 | 0.38 | 345.5 |
| Blue-green algae | Calothrix parasitica | 0.09 | 0.41 | 455.6 |
| Euglena algae | Euglena mutabilis | 0.12 | 0.19 | 158.3 |
| Brown algae | Acinetospora crinita | 0.1 | 0.18 | 180.0 |

TABLE 3-continued

| | | Absorbance | | Cell |
| Classification of Algae | Species Name | After 6 hours | After 3 days | Increase Rate |
|---|---|---|---|---|
| Green algae | Chlamydomonas kuwadae | 0.09 | 0.39 | 433.3 |
| Conjugating algae | Closterium ehrenbergii | 0.08 | 0.14 | 175.0 |
| Dinoflagellate algae | Pyrocystis fusiformis | 0.09 | 0.13 | 144.4 |

<Recovery Conditions>

Preferred recovery conditions in the method for recovering microplastics from water to be treated containing the microplastics will now be described.

(Relationship between Microplastic Concentration and Algal Concentration)

The preferred algal concentration in the system varies depending on the microplastic concentration, the size of the microplastics, the type of algae used, and others. This condition setting can be determined, for example, by carrying out the model experiments described in Examples.

(Recovery Time)

The preferred recovery time in the system varies depending on the microplastic concentration, the size of the microplastics, the type of algae to be used, the microplastic concentration to be reduced, and others. This condition setting can be determined, for example, by carrying out the model experiments described in Examples.

<<Algal Composition>>

The algae used in the methods and systems according to the present invention may be an algal composition. Specifically, the composition is a group of algae of the same or different species. For example, the group of algae is preferably stored in a container or others in a state in which the algae are viable (e.g., in a liquid medium). Freeze-dried viable algae may be handled in a dry form. Note that, if necessary, the composition may contain components other than algae.

<<Microplastic Recovery System>>

Figure 12:
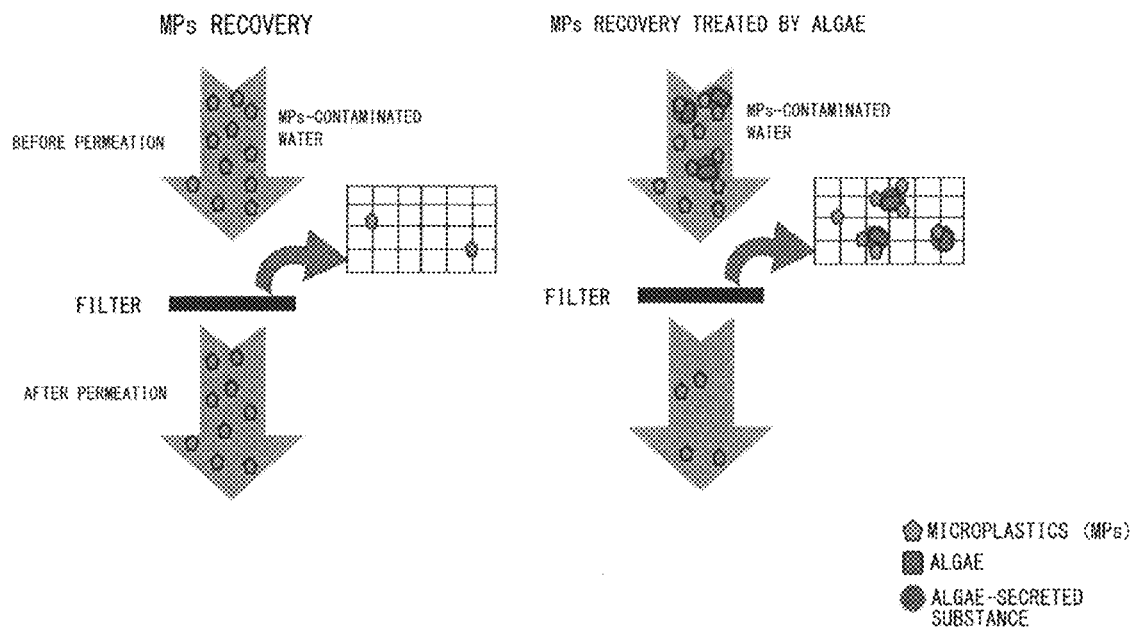
FIG. 12 is a diagram illustrating a difference between a conventional recovery system using a filtration device (filter or others) and a recovery system of an embodiment of the present invention.
Figure 14:
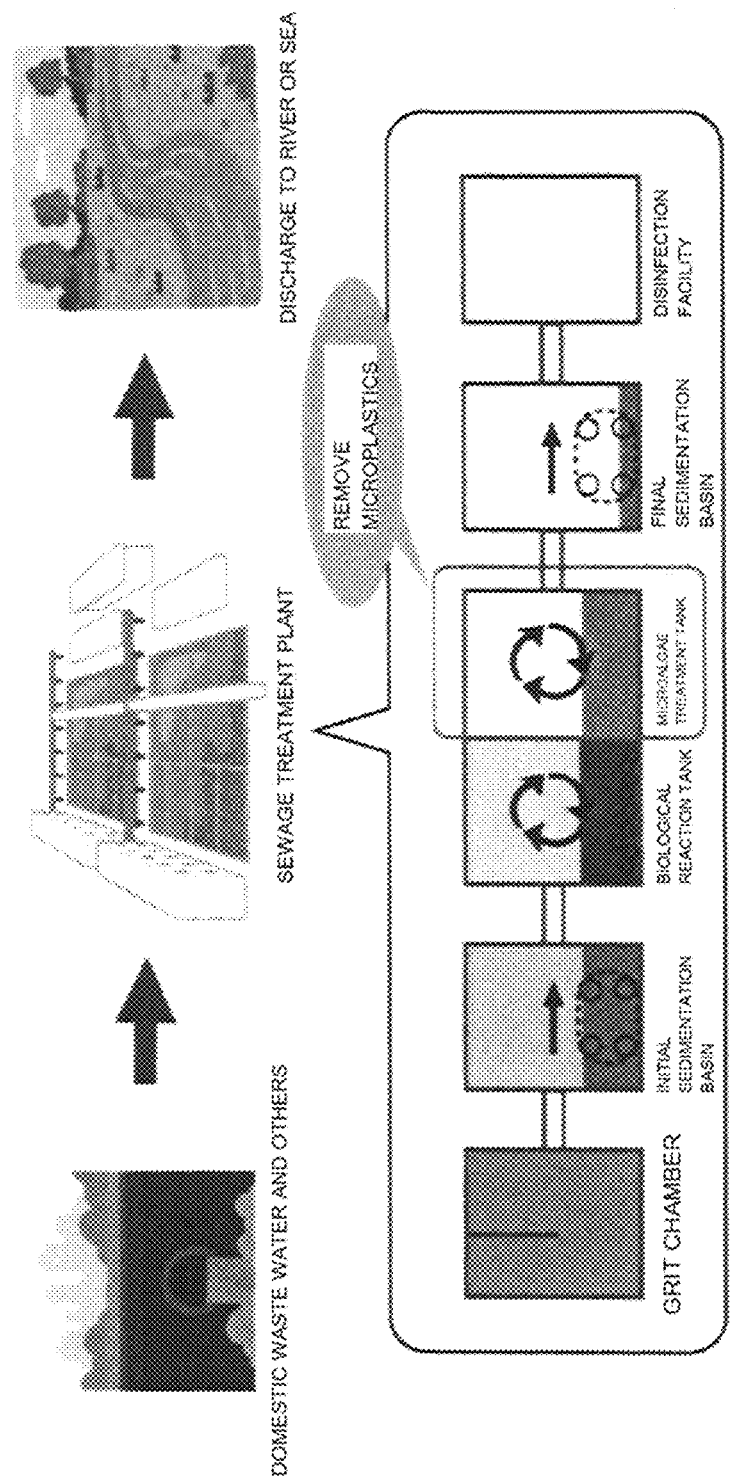
FIG. 14 is a conceptual diagram when the present invention is utilized for sewage treatment.

A microplastic recovery system according to the present embodiment will now be described. Note that a "system" as used in the present description and claims is a concept including a device and a plant. First, the system is not particularly limited if the system is characterized by using algae having microplastic adsorption and recovery ability (or algae secreting sticky substances) when recovering the microplastics from water to be treated, and various systems are assumed (e.g., FIG. 14 is a conceptual diagram when the present invention is utilized for sewage treatment). FIG. 12 is merely an example, and illustrates a difference between a conventional recovery system and the recovery system of one embodiment of the present invention, using a filtration device (filter or others). As can be seen from the figure, the conventional technique can recover only a small amount of microplastics, whereas the embodiment of the present invention can recover a larger amount of microplastics because microplastics adhere to algae and forms a lump. An example of the system will be described below.

<System Configuration>

FIG. 1 is a conceptual diagram illustrating an example of a microplastic recovery system. As illustrated in FIG. 1, the system 1 includes a microplastic recovery unit 1-1 that can store water, an algae introduction unit 1-2 that introduces water containing algae into the microplastic recovery unit 1-1, a water-to-be-treated introduction unit 1-3 that introduces water-to-be-treated that may contain microplastics into the microplastic recovery unit 1-1, and a filtration unit 1-4 that filters water treated in the microplastic recovery unit 1-1 to remove algae and others.

Note that it is preferable that a mechanism for supplying air to the microplastic recovery unit 1-1 is installed so that air can be appropriately supplied to water stored in the microplastic recovery unit 1-1. Thus, the amount of the sticky substances secreted from algae cultured in the water stored in the microplastic recovery unit 1-1 is increased, and thus the amount of the microplastic adsorbed and recovered by algae can be increased.

<System Function>

Figure 2:
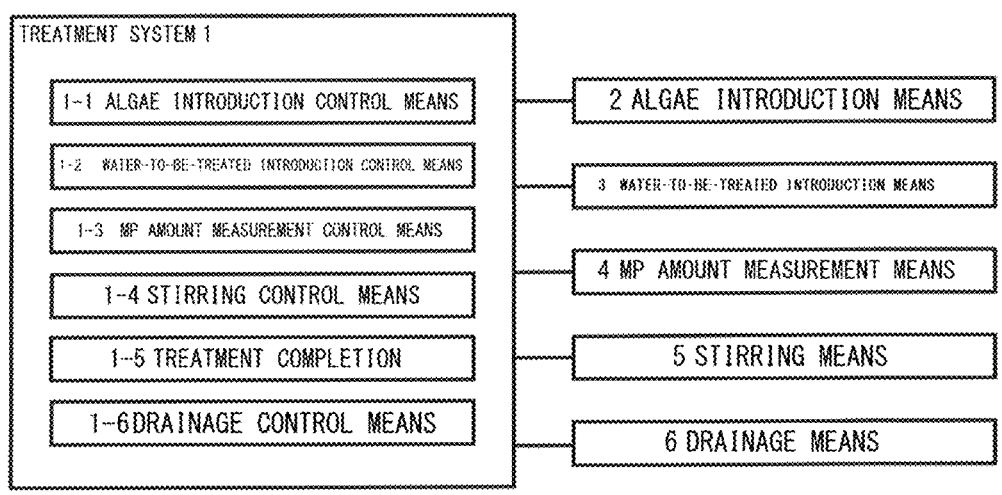
FIG. 2 is an example of a control block diagram of the microplastic recovery system.

Then, FIG. 2 is an example of a control block diagram of the microplastic recovery system. The treatment system 1 includes an algae introduction control means 1-1 that controls an algae introduction means 2 to control introduction of water containing algae into the microplastic recovery unit 1-1, a water-to-be-treated introduction control means 1-2 that controls a water-to-be-treated introduction means 3 to control introduction of water to be treated into the microplastic recovery unit 1-1, an MP amount measurement control means 1-3 that controls a MP amount measurement means that measures the presence and/or amount of plastics in the microplastic recovery unit 1-1, a stirring control means 1-4 that controls stirring of a stirring means 5 that stirs water (water to be treated+algae) in the microplastic recovery unit 1-1, a treatment completion determination means 1-5 that determines whether treatment of water to be treated is completed, and a drainage control means 1-6 that controls drainage of a drainage means 6 that drains the water to be treated from the microplastic recovery unit 1-1 after treatment of water to be treated.

<Control>

Figure 3:
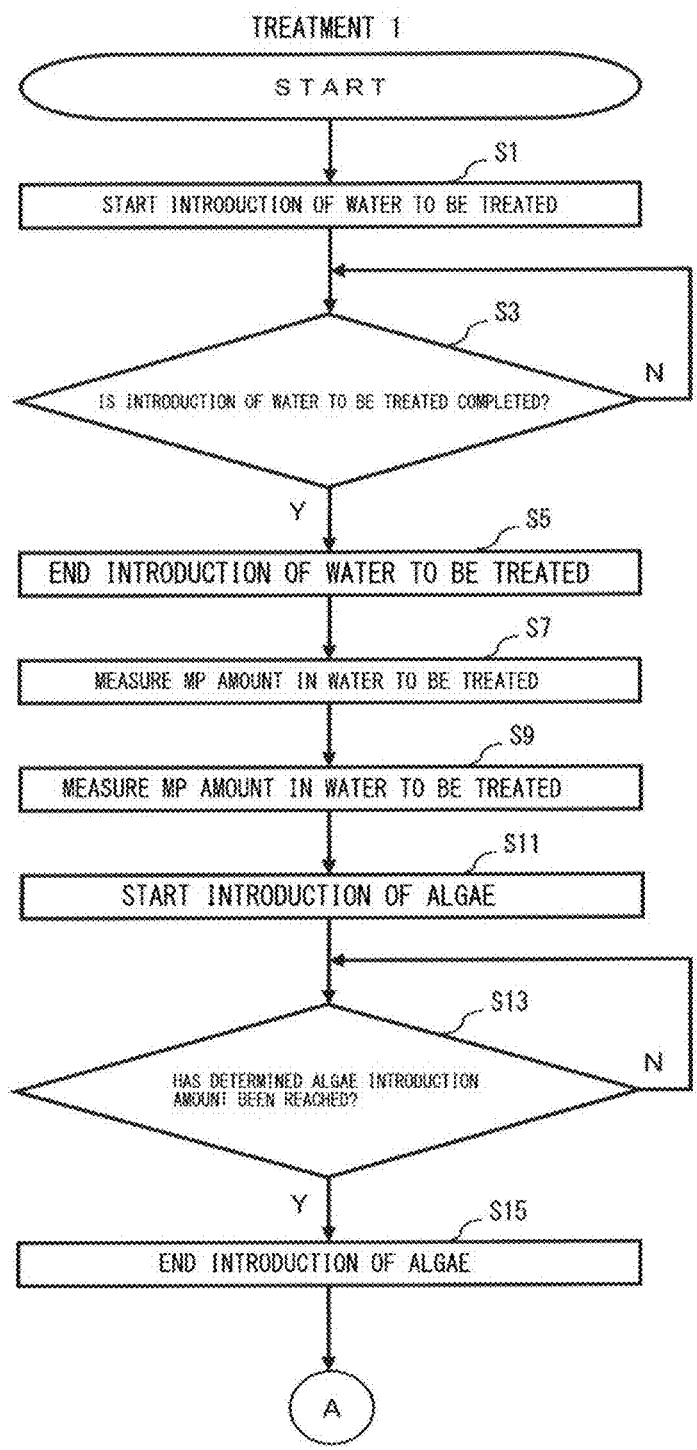
FIG. 3 is an example of a control flow diagram in the microplastic recovery system.
Figure 4:
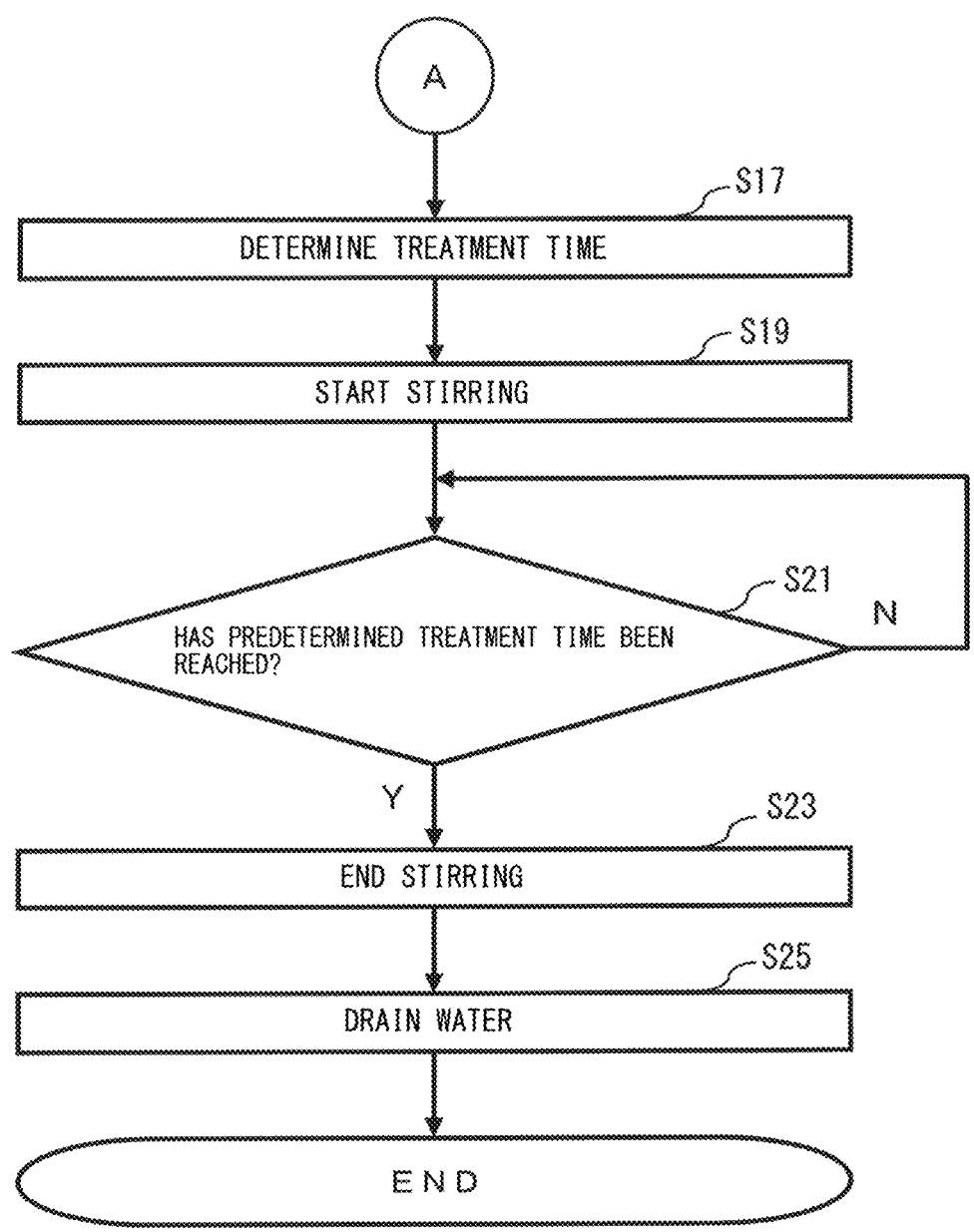
FIG. 4 is an example of a control flow diagram in the microplastic recovery system.

Then, FIGS. 3 and 4 are examples of control flow diagrams in the microplastic recovery system. First, in step 1, the water-to-be-treated introduction control means 1-2 controls the water-to-be-treated introduction means 3 to start introduction of the water to be treated into the microplastic recovery unit 1-1. Then, in step 3, the water-to-be-treated introduction control means 1-2 determines whether or not a predetermined amount of water to be treated has been introduced into the microplastic recovery unit 1-1. If Yes in step 3, the water-to-be-treated introduction control means 1-2 controls the water-to-be-treated introduction means 3 to complete the introduction of the water to be treated into the microplastic recovery unit 1-1. Note that, if No in step 3, the introduction of the water to be treated is continued. Then, in step 7, the MP amount measurement control means 1-3 performs measurement control of the MP amount in the microplastic recovery unit 1-1 using the MP amount measurement means 4. In step 9, the MP amount measurement control means 1-3 determines the amount of algae to be introduced into the microplastic recovery unit 1-1 according to the amount of microplastics in the water to be treated. Then, in step 11, the algae introduction control means 1-1 controls the algae introduction means 2 to start introduction of water containing algae into the microplastic recovery unit 1-1 from, for example, an algae storage unit {e.g., a storage unit storing water containing algae (e.g., fresh water or seawater) and having, for example, a function of culturing algae} provided separately from the microplastic recovery unit 1-1. Then, in step 13, the algae introduction control means 1-1 determines whether or not the algae introduction amount determined in step 9 has been reached. If Yes in step 13, in step 15, the algae introduction control means 1-1 ends introduction of algae into the microplastic recovery unit 1-1 from the algae storage unit. Note that, if No in step 13, the introduction of algae is continued. Then, in step 17, the stirring control means 1-4 determines the stirring time (treatment time) based on a predetermined parameter (e.g., microplastic concentration or amount of introduced algae) for determining the stirring time for making the microplastic amount or concentration less than or equal to a predetermined amount. In step 19, the stirring control means 1-4 controls the stirring means 5 to start stirring of the water (water containing microplastics +algae) in the microplastic recovery unit 1-1. Then, in step 21, the stirring control means 1-4 determines whether or not the stirring time (treatment time) determined in step 17 has been reached. If Yes in step 21, the stirring control means 1-4 controls the stirring means 5 to end stirring of water in the microplastic recovery unit 1-1. Note that, if No in step 21, the stirring of the water in the microplastic recovery unit 1-1 is continued. Then, in step 25, the drainage control means 1-6 controls the drainage means 6 to drain the water (treated water) in the microplastic recovery unit 1-1. Note that the drainage is then preferably introduced into the filtration unit, where microplastic-attached algae are removed from the water.

As a result, the water contaminated with microplastics can be turned into water that contains no microplastics or contains a reduced amount of microplastics.

<Other Control Example 1>

Figure 5:
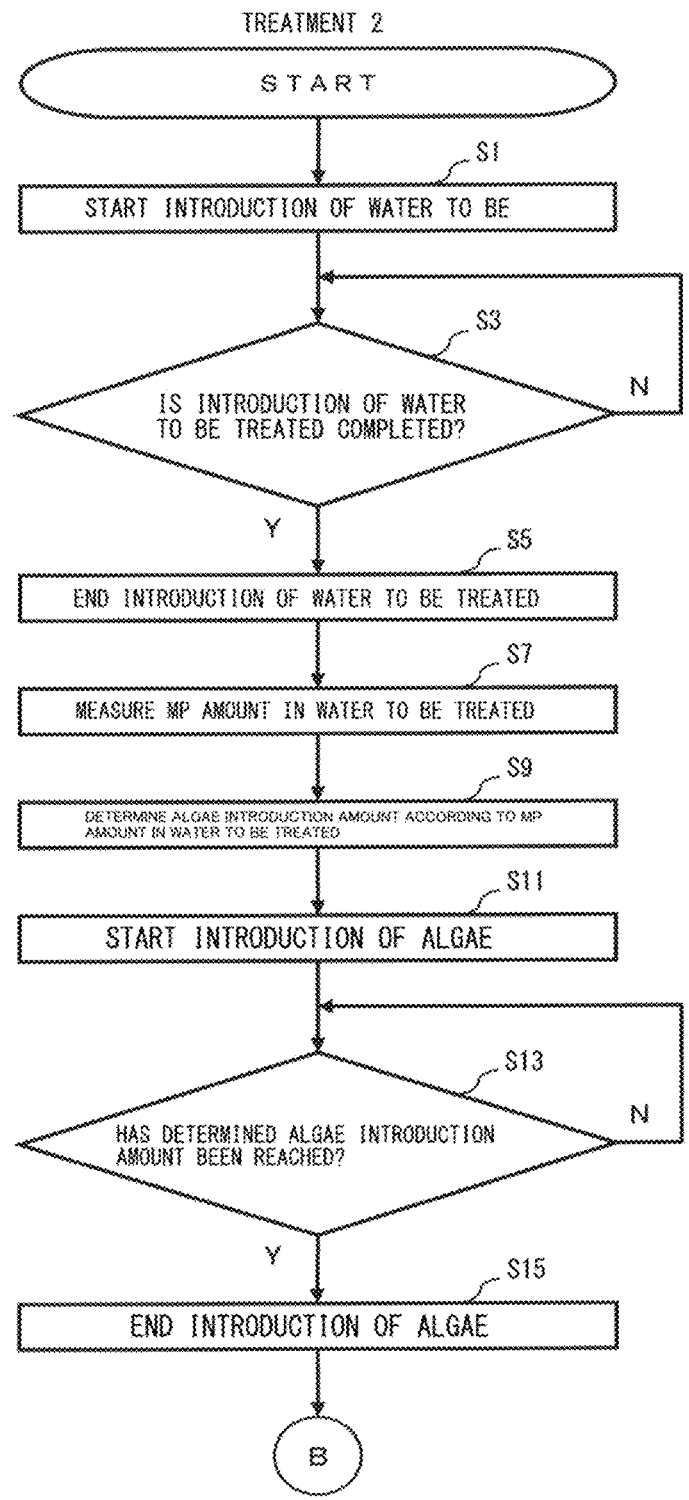
FIG. 5 is an example of a control flow diagram in another system capable of executing control different from the control in FIG. 4.
Figure 6:
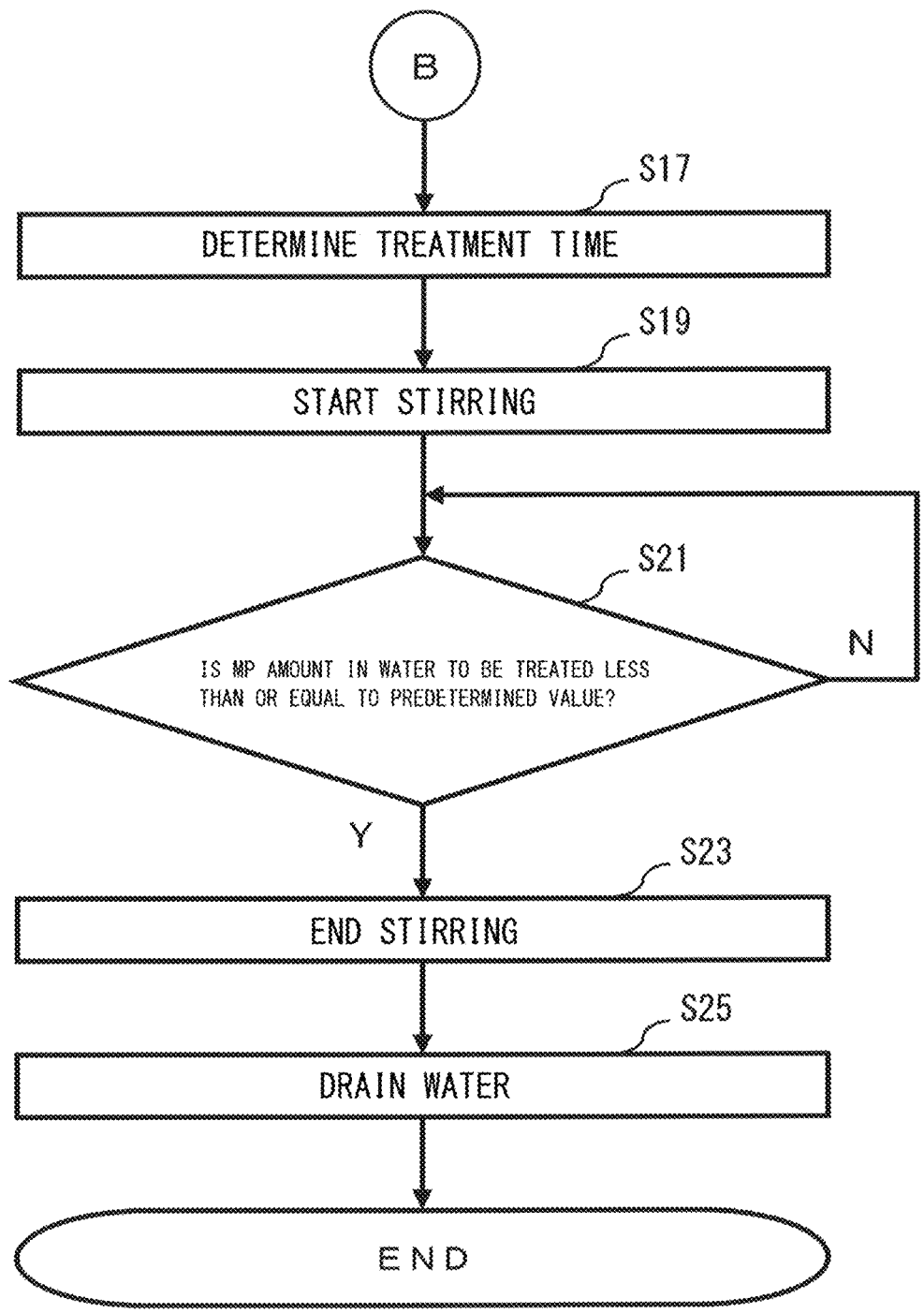
FIG. 6 is an example of a control flow diagram in another system capable of executing control different from the control in FIG. 4.

FIGS. 5 and 6 are examples of control flow diagrams in another system capable of executing control different from the control described above. The control in these figures is different from the above-described control, and the difference is the process in step 21. In the above-described control, the stirring control means 1-4 executes a process of determining whether or not the determined stirring time (treatment time) determined in step 17 has been reached. On the other hand, in the control in these figures, the stirring control means 1-4 measures the presence or absence or the amount of microplastics in the microplastic recovery unit 1-1 using the MP amount measurement means 4 and determines whether or not the MP amount in the water to be treated is less than or equal to a predetermined amount.

<Other Control Example 2>

Figure 7:
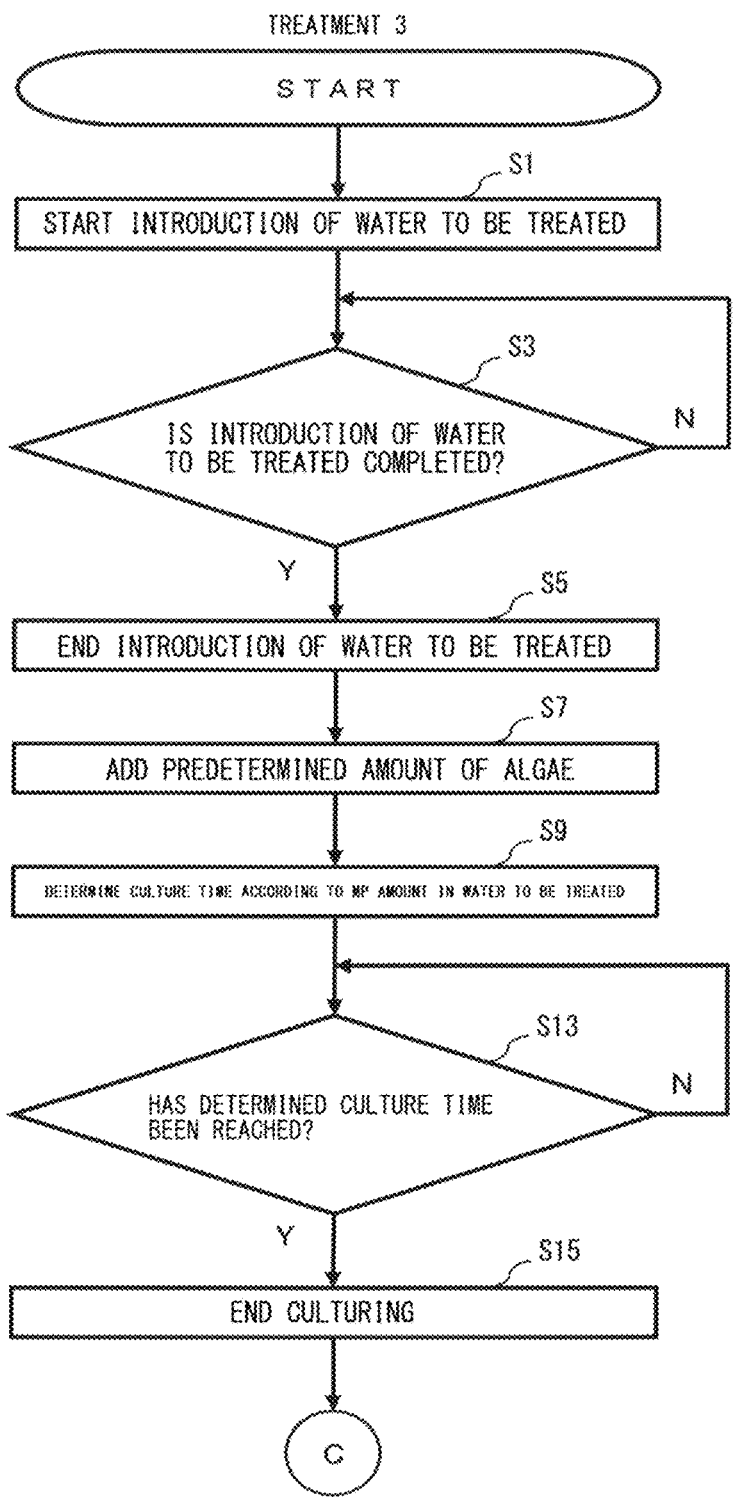
FIG. 7 is an example of a control flow diagram in still another system capable of executing control different from the control in FIG. 4.
Figure 8:
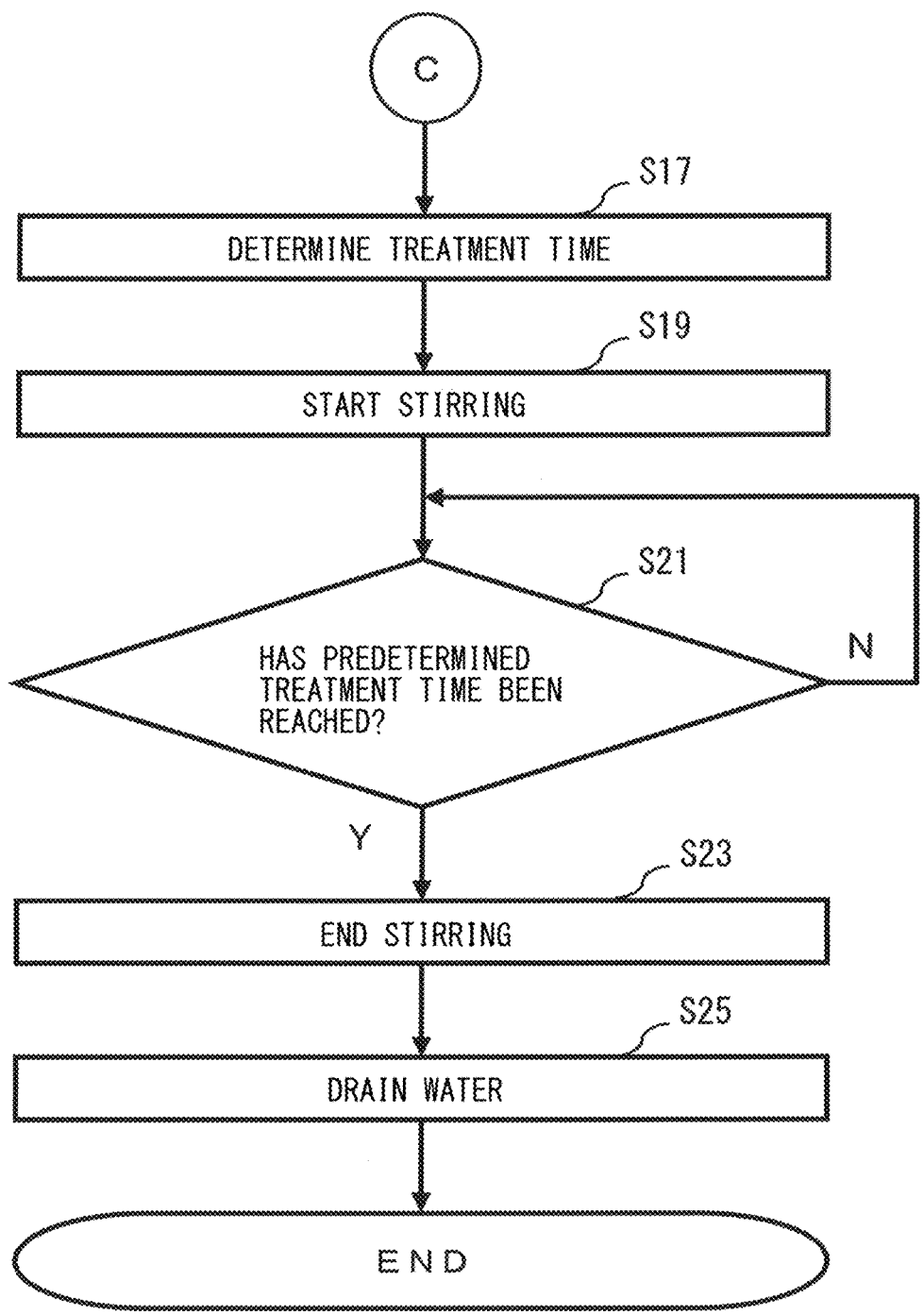
FIG. 8 is an example of a control flow diagram in still another system capable of executing control different from the control in FIG. 4.

FIGS. 7 and 8 are examples of control flow diagrams in still another system capable of executing control different from the control described above. The above-described system is a system in which a predetermined amount of algae (an amount of algae according to the amount of microplastics contained in water introduced into the microplastic recovery unit 1-1) is introduced into the microplastic recovery unit 1-1. On the other hand, this system is different from the above-described system in that sufficient algae for treating microplastics contained in water introduced into the microplastic recovery unit 1-1 are allowed to be present in the microplastic recovery unit 1-1 by introducing algae into the microplastic recovery unit 1-1 (an amount of algae smaller than an amount of algae capable of treating microplastics contained in water introduced into the microplastic recovery unit 1-1) and then culturing the algae in the microplastic recovery unit 1-1. Based on the difference, the process of this system is explained as follows. In step 7, the algae introduction control means 1-1 controls the algae introduction means 2 to add a predetermined amount of algae into the microplastic recovery unit 1-1. Then, in step 9, the MP amount measurement control means 1-3 controls the MP amount measurement means 4 to measure the presence and/or amount of microplastics in the microplastic recovery unit 1-1, and then the treatment system 1 determines the culture conditions of the algae based on the "amount of microplastics in the water to be treated" and the "amount of introduced algae" (time, temperature, and others). Note that, in this example, the culture condition is described by taking time as an example. Then, in step 13, the treatment system 1 determines whether or not the culture time determined in step 9 has been reached. If Yes in step 13, in step 15, the treatment system 1 ends culturing of the algae in the microplastic recovery unit 1-1. On the other hand, if No in step 13, the culturing of the algae is continued.

<<Utility>>

Figure 13:
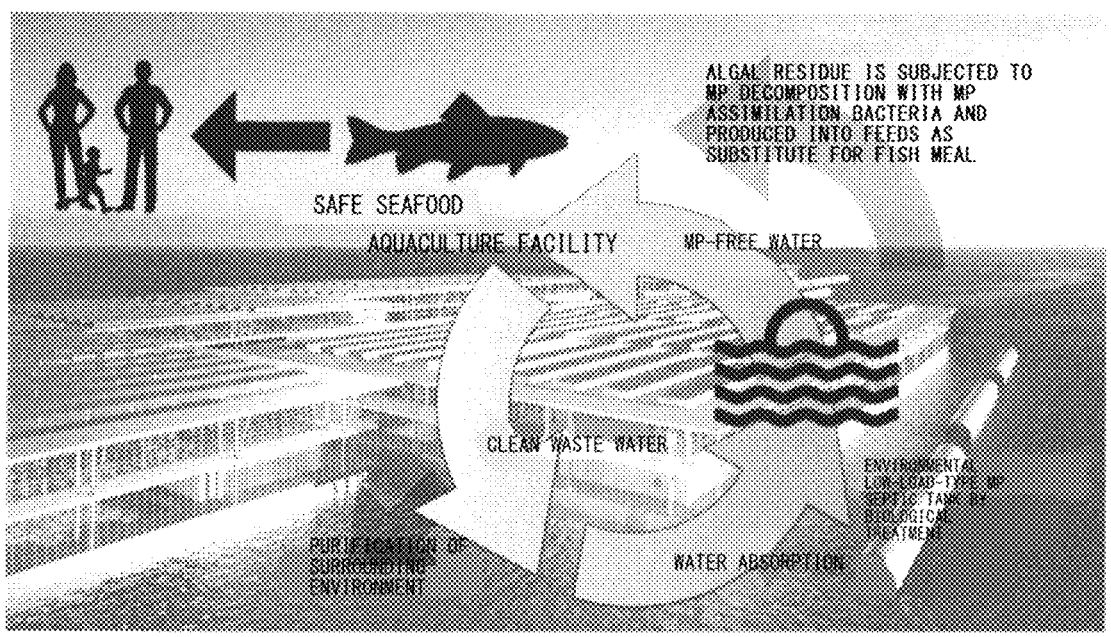
FIG. 13 is a diagram illustrating an example of utilization of algae used for microplastic recovery.

The present invention is useful in producing non-microplastic marine seafood and safe and secure seafood, which are equivalent to non-pesticide (organic) agricultural products on land. In particular, the present invention is promising for introduction into on-land aquaculture facilities because microplastics in the environment are not ingested. Examples thereof include cultivation of sea grapes, seaweed laver, Malabar grouper (high-class fish), oysters, sea urchins, and shrimps. Further, the present invention leads to an environmental contribution of removal of coastal MP for consumers. In addition, the algae used for microplastic recovery can also be utilized in the application illustrated in FIG. 13.

EXAMPLES

<<Culture of Algae>>

The algae used in the experiment (see Table 4) were cultured on a 1 L scale. At this point, the turbidities were measured and recorded using a turbidimeter (CO8000 Biowave). For example, the number of algal cells was 7000 cells/ml for algae of the genus Skeletonema or having a size of about 5 to 10 μm. Note that, if the number of algal cells was more than 7000 cells/ml, the algae were diluted with medium or others. On the other hand, if the number of algal cells was less than 7000 cells/ml, supernatant was removed after 2 to 3 hours for adjustment. Then, 19.648 ml of well-suspended culture solution was placed in a 70 ml cell culture flask (three flasks were prepared). As a control, 19.648 ml of medium was placed in a new 70 ml cell culture flask {four flasks were prepared (one of the four flasks was used for preparing a calibration curve)}. In addition, about 20 ml of well-suspended culture solution was prepared for base-line correction when the absorbance was measured with an ultraviolet-visible spectrophotometer. Then, 352 μl of a 2 μm bead solution ($5.68 \times 10^8$ beads/ml) was placed in a 70 ml cell culture flask containing the culture solution. The solution was then mixed by pipetting, and placed in an artificial meteorological device at 20° C. for static culture (for 1 day). Note that FIG. 11 is enlarged photographs of various algae used. In the figure, the dotted lines indicate the cell surface, and the solid lines indicate the interface of the sticky substance. Table 5 illustrates the amounts of the sticky components calculated by the method described in the general description.

TABLE 4

| Classification of Algae | Species Name | Size |
| --- | --- | --- |
| Diatoms | Achnanthes kuwaitensis | 12-40 μm |
| | Skeletonema tropicum | 3-12 μm |
| Blue-green algae | Calothrix parasitica | –11 μm |
| Euglena | Euglena mutabilis | –63 μm |
| Brown algae | Acinetospora crinita | 17 μm |
| Green algae | Chlamydomonas kuwadae | 10-25 μm |
| Conjugating algae | Closterium ehrenbergii | 80-500 μm |
| Dinoflagellate algae | Pyrocystis fusiformis | 400 μm |

TABLE 4-continued

| Classification of Algae | Species Name | Size |
| --- | --- | --- |

TABLE 5

| Classification of Algae | Species used in Analysis | Amount of Mucilage |
| --- | --- | --- |
| Diatoms | Achnanthes kuwaitensis | 5 times |
| | Skeletonema tropicum | 10 times |
| Blue-green algae | Calothrix parasitica | 35 times |
| Euglena | Euglena mutabilis | 1 times |
| Brown algae | Acinetospora crinita | — (not confirmed) |
| Green algae | Chlamydomonas kuwadae | 7 times |
| Conjugating algae | Closterium ehrenbergii | 12 times |
| Dinoflagellate algae | Pyrocystis fusiformis | 0.39 times |

<<Microplastic Recovery Test>>

Figure 9:
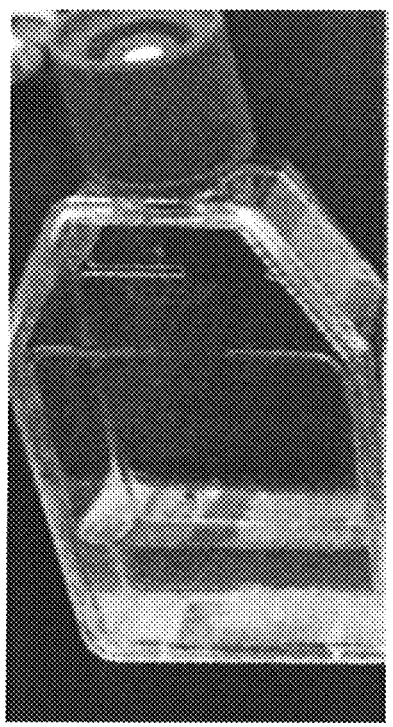
FIG. 9 is a diagram (photograph) illustrating a state in which precipitates were confirmed after adsorption of microplastics in Examples.

The flask {solution with a final concentration of $1 \times 10^7$ beads (2 μm)/ml in which the above each algae was cultured} obtained in the above-described <<Culture of Algae>> was taken out from the artificial meteorological device so as not shake the flask. At this point, as illustrated in FIG. 9, precipitates were confirmed. The solution was then suspended by swirling and pipetting. Then, a 50 μm cell strainer (pluriStrainer 50 μm) was set and labeled in a 50 ml tube using a connector ring (cell strainers corresponding to the number of cell culture flasks other than those for the calibration curve were prepared). All culture flasks were depressurized and filtered, in each cell strainer, using a syringe (culture flasks for calibration curves were not filtered). The primarily filtered samples were then covered with a lid and stored on a laboratory table. A calibration curve was prepared, and then a beads dilution series for a calibration curve was prepared in order to estimate the beads recovery rate by algae. Specifically, medium to which beads were not added was set to be a beads concentration of 0, and 1/2 dilution was repeated from a stock concentration of $1.00 \times 10^7$ beads/ml to prepare $3.13 \times 10^5$ beads/ml, $6.25 \times 10^5$ beads/ml, $1.25 \times 10^6$ beads/ml, $2.50 \times 10^6$ beads/ml, and $5.00 \times 10^6$ beads/ml.

<<Microplastic Recovery Measurement Test>>

The absorbance at 267 nm, which is the fluorescence of the beads, was measured using an ultraviolet-visible spectrophotometer, BioSpec-Mini (Shimadzu Corporation). At this point, in order to estimate the beads recovery rate of the algae, the beads dilution series for a calibration curve was measured, and a calibration curve was prepared to obtain a primary regression equation. A 50 μm cell-strainer permeated solution of the algae culture medium+beads solution was used as a sample to measure absorbance, and the beads concentration in the permeated solution was calculated from the primary regression equation obtained by the calibration curve. In the same manner, a 50 μm cell strainer permeated solution of the medium+beads solution without culture was used as a control to measure absorbance, and the beads concentration in the permeated solution was calculated from the primary regression equation obtained by the calibration curve. The recovery rate of the beads was calculated from the beads concentration in the sample and the beads concentration in the control. The results are illustrated in Table 6.

TABLE 6

| Classification of Algae | Species used in Analysis | Recovery Rate of Treatment Time 1 Day |
|---|---|---|
| Diatoms | Achnanthes kuwaitensis | 25% |
|  | Skeletonema tropicum | 40% |
| Blue-algae | Calothrix parasitica | 38% |
| Euglena | Euglena mutabilis | 18% |
| Brown algae | Acinetospora crinita | 10% |
| Green algae | Chlamydomonas kuwadae | 6% |
| Conjugating algae | Closterium ehrenbergii | 5% |
| Dinoflagellate algae | Pyrocystis fusiformis | 17% |

Remarks: Recovery rate of conjugating algae: performed at cell number of 240 cells/ml
Recovery rate of brown algae: performed at cell number of 106 cells/ml and recovery time 4 hrs
Recovery rate of green algae: performed at recovery time 4 hrs

The invention claimed is:

1. A method for recovering microplastics from water to be treated containing the microplastics, the method comprising a step of allowing algae having microplastic adsorption and recovery ability to be present in the water to be treated, wherein
the algae secrete a sticky substance, and
the method further comprises a culture step of causing the algae to secrete the sticky substance such that a volume of the sticky substance secreted to an outside of cells of the algae is 0.25 times or more and 100 times or less compared to a cell volume of the algae.

2. The method according to claim 1, wherein the sticky substance is a polysaccharide.

3. The method according to claim 1, wherein
the algae are at least one species selected from diatoms, dinoflagellate algae, Chlorarachniophyte algae, green algae, red algae, conjugating algae, Euglena algae, and blue-green algae.

4. A system for recovering microplastics from water to be treated containing the microplastics, the system utilizing algae having microplastic adsorption and recovery ability when the microplastics are recovered from the water to be treated, wherein
the algae secrete a sticky substance, and
the system further comprises a culture unit that causes the algae to secrete the sticky substance such that a volume of the sticky substance secreted to an outside of cells of the algae is 0.25 times or more and 100 times or less compared to a cell volume of the algae.

5. The system according to claim 4, wherein the sticky substance is a polysaccharide.

6. The system according to claim 4, wherein the algae are at least one species selected from diatoms, dinoflagellate algae, Chlorarachniophyte algae, green algae, red algae, conjugating algae, Euglena algae, and blue-green algae.

* * * * *